US012690843B2

(12) United States Patent
Imura et al.

(10) Patent No.: US 12,690,843 B2
(45) Date of Patent: Jul. 28, 2026

(54) KEY FRAME IDENTIFICATION FOR INTRAVASCULAR ULTRASOUND BASED ON PLAQUE BURDEN

(71) Applicant: BOSTON SCIENTIFIC SCIMED, INC., Maple Grove, MN (US)

(72) Inventors: Haruka Imura, Maple Grove, MN (US); Judith Tiferes Wang, Buenos Aires (AR); Wenguang Li, Los Gatos, CA (US); Erik Stephen Freed, New Brighton, MN (US); Jennifer Gibbs, White Bear, MN (US); Anming He Cai, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 51 days.

(21) Appl. No.: 18/367,874

(22) Filed: Sep. 13, 2023

(65) Prior Publication Data

US 2024/0081785 A1    Mar. 14, 2024

Related U.S. Application Data

(60) Provisional application No. 63/406,361, filed on Sep. 14, 2022.

(51) Int. Cl.
*A61B 8/00* (2006.01)
*A61B 8/08* (2006.01)
*A61B 8/12* (2006.01)

(52) U.S. Cl.
CPC ............ *A61B 8/469* (2013.01); *A61B 8/0891* (2013.01); *A61B 8/12* (2013.01); *A61B 8/5207* (2013.01); *A61B 8/5223* (2013.01)

(58) Field of Classification Search
CPC ......... A61B 8/469; A61B 8/0891; A61B 8/12; A61B 8/5207; A61B 8/5223; A61B 5/02007; A61B 5/1076; A61B 8/463; A61B 8/461; A61B 8/5215; G06T 7/0012; G06T 7/13; G06T 7/62; G06T 2207/10016;

(Continued)

(56) References Cited

U.S. PATENT DOCUMENTS

| | | |
|---|---|---|
| 6,945,938 B2 | 9/2005 | Grunwald |
| 7,246,959 B2 | 7/2007 | Nakatani |

(Continued)

FOREIGN PATENT DOCUMENTS

| | | |
|---|---|---|
| JP | 2016503310 A | 2/2016 |
| JP | 2020114423 A | 7/2020 |

(Continued)

OTHER PUBLICATIONS

International Search Report and Written Opinion dated Dec. 5, 2023 for International Application No. PCT/US2023/032642.

(Continued)

*Primary Examiner* — Kaitlyn E Sebastian
(74) *Attorney, Agent, or Firm* — Seager Tufte & Wickhem, LLP

(57) ABSTRACT

The present disclosure provides to process intravascular ultrasound (IVUS) images to identify key frames such as the proximal key frame, a distal key frame, and a minimal key frame from the IVUS images based on the raw lumen area, vessel area, and plaque burden. Ones of the key frames can be re-identified based on manipulation of other ones of the key frames.

20 Claims, 11 Drawing Sheets

(58) Field of Classification Search
CPC .......... G06T 2207/10132; G06T 2207/30101;
G06V 10/25
See application file for complete search history.

(56) References Cited

U.S. PATENT DOCUMENTS

| | | | |
|---|---|---|---|
| 7,306,561 B2 | 12/2007 | Sathyanarayana | |
| 2006/0100522 A1 | 5/2006 | Yuan et al. | |
| 2006/0106320 A1 | 5/2006 | Barbato | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |
| 2010/0150413 A1* | 6/2010 | Futamura | G06T 7/0012 |
| | | | 382/128 |
| 2013/0267848 A1* | 10/2013 | Fearnot | A61B 8/12 |
| | | | 606/200 |
| 2016/0206267 A1* | 7/2016 | Shimizu | A61B 8/0891 |
| 2019/0282182 A1* | 9/2019 | Scott | G16H 50/30 |
| 2020/0294659 A1 | 9/2020 | Gopinath et al. | |
| 2022/0117551 A1 | 4/2022 | Gopinath et al. | |
| 2023/0121688 A1 | 4/2023 | Begin et al. | |

FOREIGN PATENT DOCUMENTS

| | | |
|---|---|---|
| JP | 2021517034 A | 7/2021 |
| JP | 2022525469 A | 5/2022 |
| WO | 2021156215 A1 | 8/2021 |

OTHER PUBLICATIONS

Rezaei et al., "Systematic mapping study on diagnosis of vulnerable plaque," Multimedia Tools and Applications, 78:21695-21730, 2019.
Ziemer et al., "Automated lumen segmentation using multi-frame convolution neural networks in intravascular ultrasound datasets," European Heart Journal—Digital Health, 1:75-82, 2020.

* cited by examiner

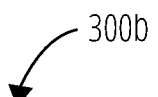
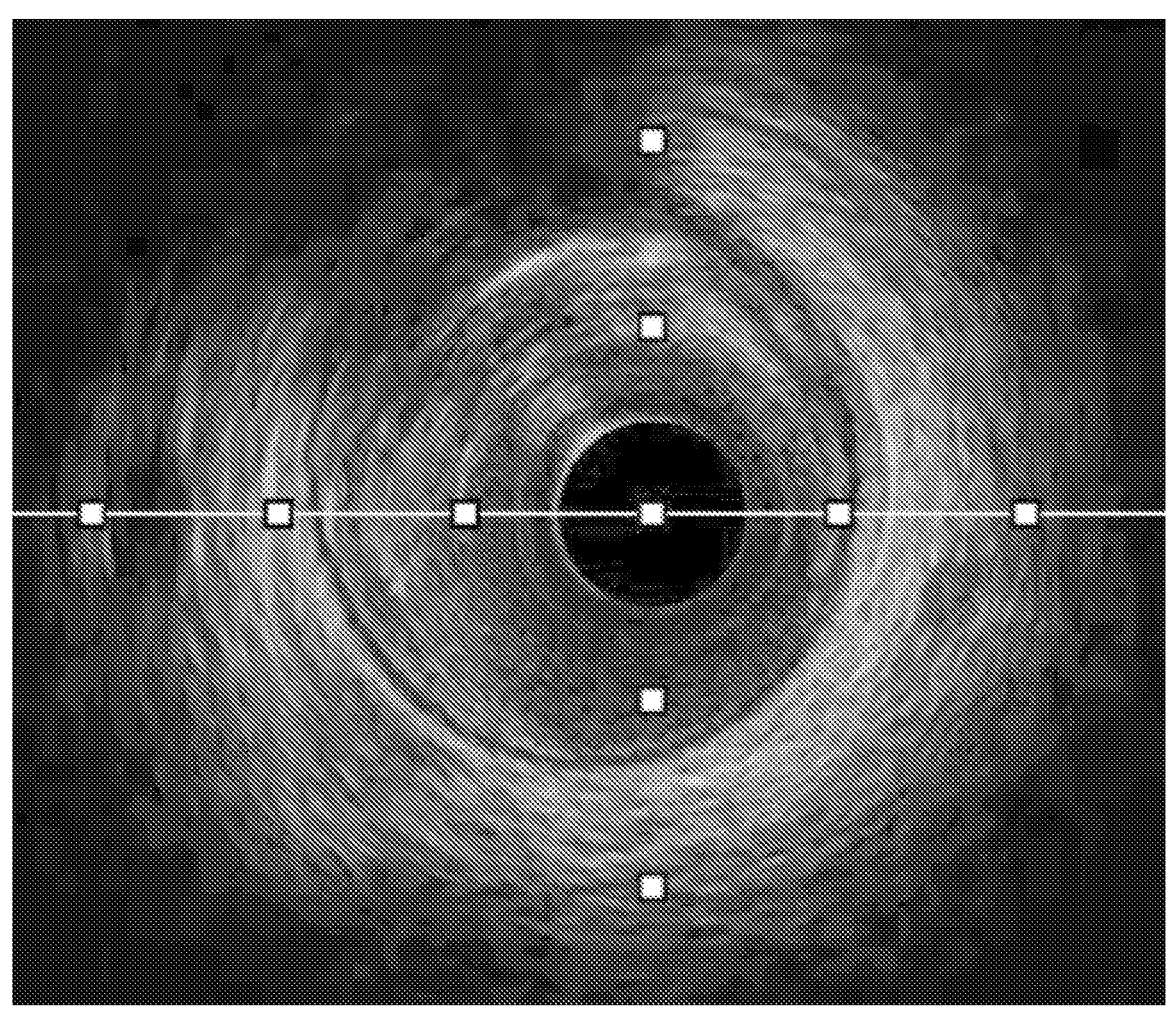
FIG. 3B

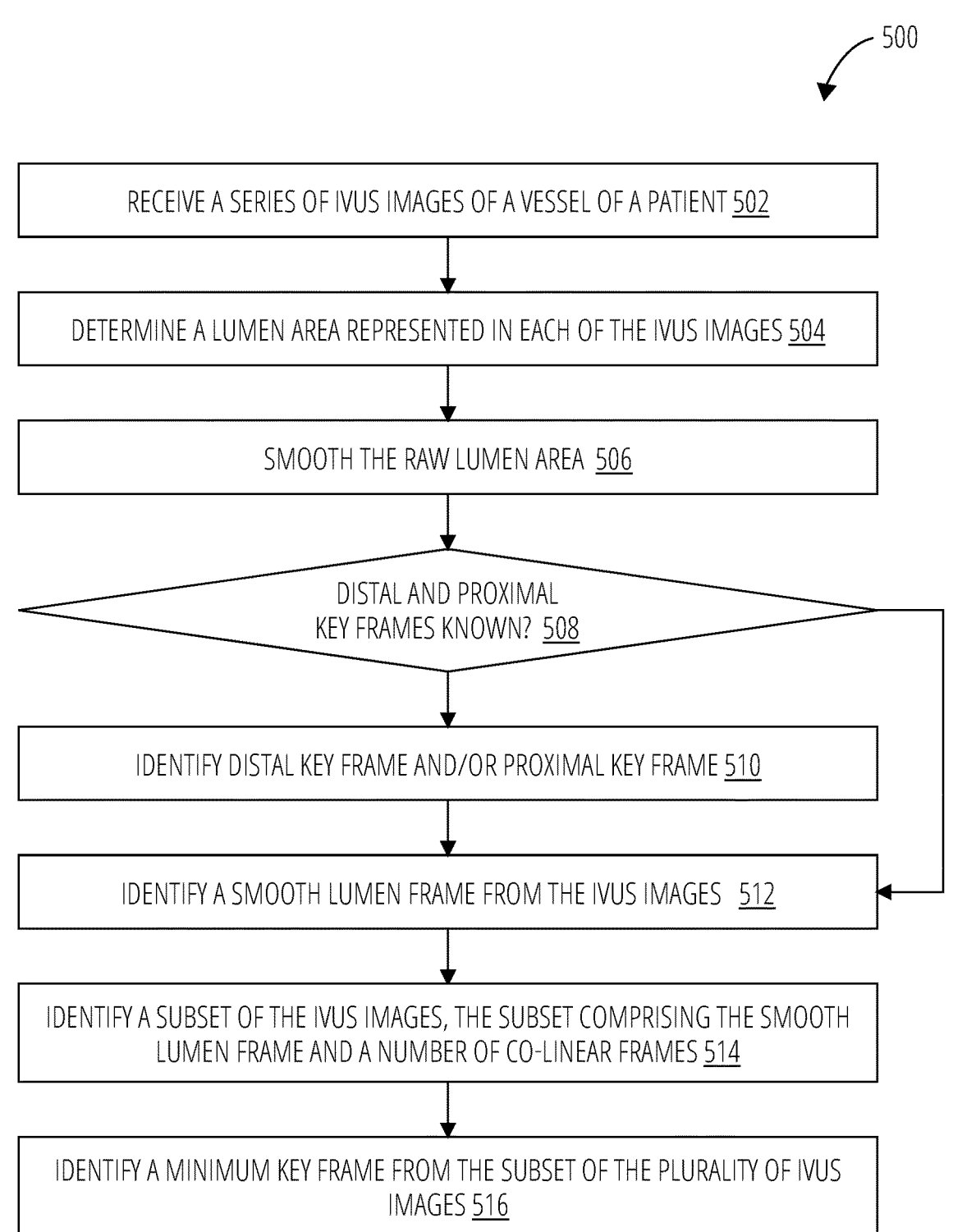

500

RECEIVE A SERIES OF IVUS IMAGES OF A VESSEL OF A PATIENT 502

DETERMINE A LUMEN AREA REPRESENTED IN EACH OF THE IVUS IMAGES 504

SMOOTH THE RAW LUMEN AREA 506

DISTAL AND PROXIMAL KEY FRAMES KNOWN? 508

IDENTIFY DISTAL KEY FRAME AND/OR PROXIMAL KEY FRAME 510

IDENTIFY A SMOOTH LUMEN FRAME FROM THE IVUS IMAGES 512

IDENTIFY A SUBSET OF THE IVUS IMAGES, THE SUBSET COMPRISING THE SMOOTH LUMEN FRAME AND A NUMBER OF CO-LINEAR FRAMES 514

IDENTIFY A MINIMUM KEY FRAME FROM THE SUBSET OF THE PLURALITY OF IVUS IMAGES 516

FIG. 5

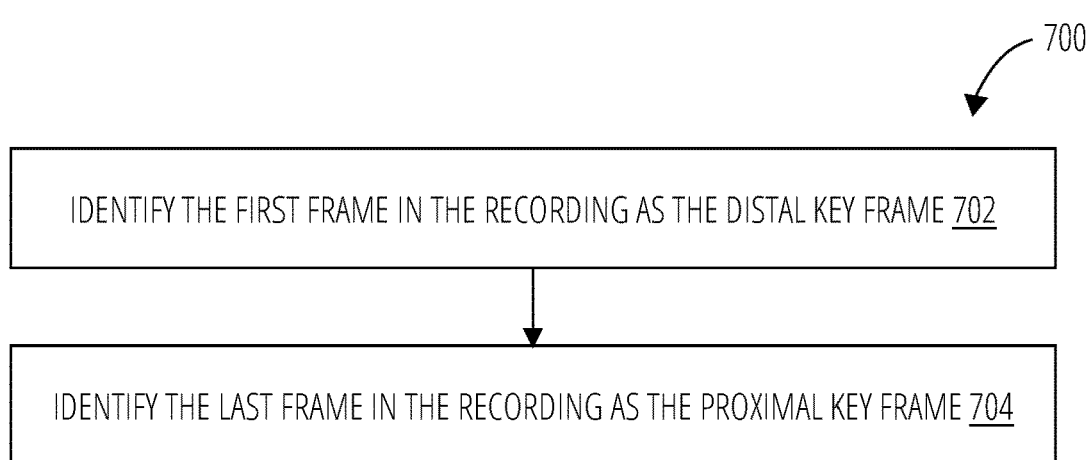

IDENTIFY THE FIRST FRAME IN THE RECORDING AS THE DISTAL KEY FRAME 702

IDENTIFY THE LAST FRAME IN THE RECORDING AS THE PROXIMAL KEY FRAME 704

FIG. 7

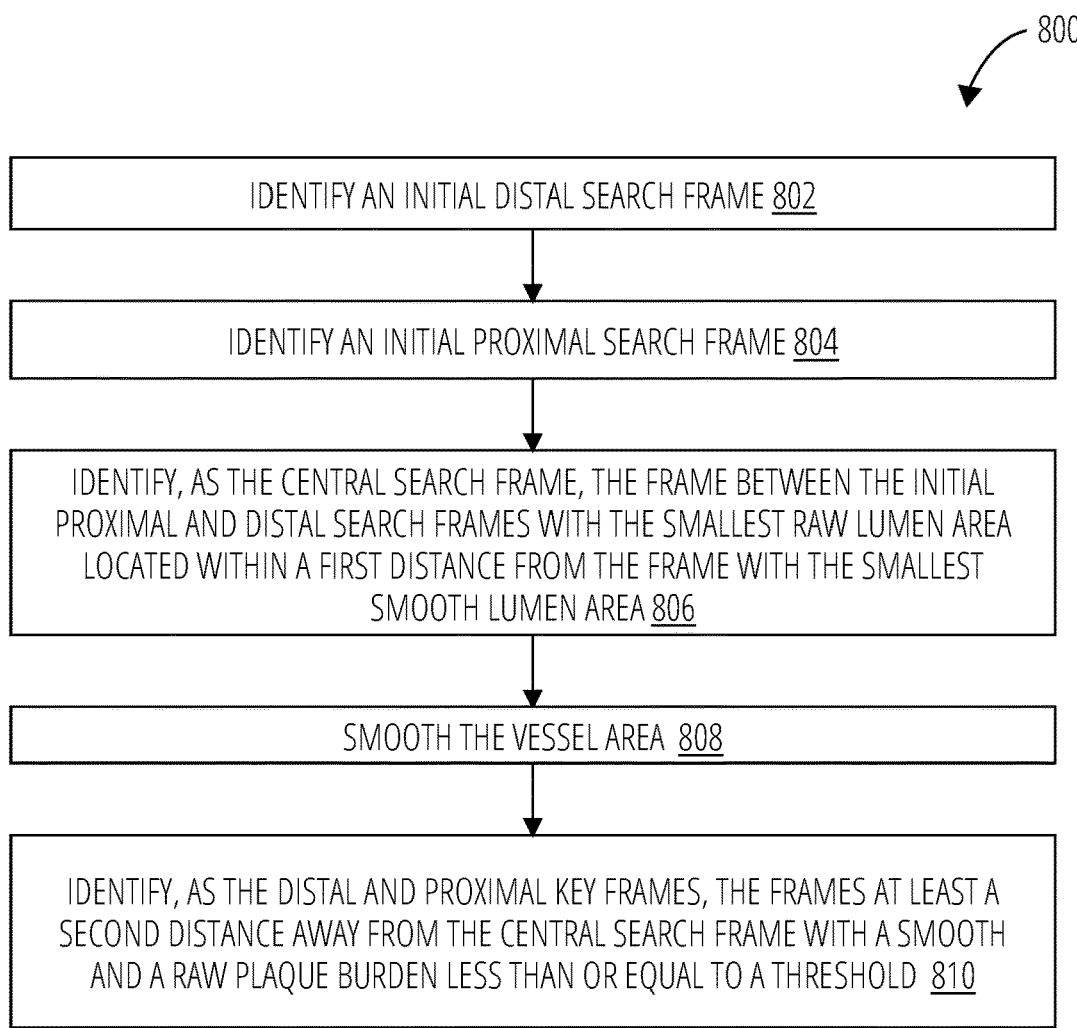

IDENTIFY AN INITIAL DISTAL SEARCH FRAME 802

IDENTIFY AN INITIAL PROXIMAL SEARCH FRAME 804

IDENTIFY, AS THE CENTRAL SEARCH FRAME, THE FRAME BETWEEN THE INITIAL PROXIMAL AND DISTAL SEARCH FRAMES WITH THE SMALLEST RAW LUMEN AREA LOCATED WITHIN A FIRST DISTANCE FROM THE FRAME WITH THE SMALLEST SMOOTH LUMEN AREA 806

SMOOTH THE VESSEL AREA 808

IDENTIFY, AS THE DISTAL AND PROXIMAL KEY FRAMES, THE FRAMES AT LEAST A SECOND DISTANCE AWAY FROM THE CENTRAL SEARCH FRAME WITH A SMOOTH AND A RAW PLAQUE BURDEN LESS THAN OR EQUAL TO A THRESHOLD 810

FIG. 8

KEY FRAME IDENTIFICATION FOR INTRAVASCULAR ULTRASOUND BASED ON PLAQUE BURDEN

CROSS-REFERENCE TO RELATED APPLICATIONS

This application claims the benefit of U.S. Provisional Patent Application Ser. No. 63/406,361 filed on Sep. 14, 2022, the disclosure of which is incorporated herein by reference.

TECHNICAL FIELD

The present disclosure generally relates to intravascular ultrasound (IVUS) imaging system. Particularly, but not exclusively, the present disclosure relates to identifying key frame markers using the plaque burden represented in IVUS images.

BACKGROUND

Ultrasound devices insertable into patients have proven diagnostic capabilities for a variety of diseases and disorders. For example, intravascular ultrasound (IVUS) imaging systems have been used as an imaging modality for diagnosing blocked blood vessels and providing information to aid medical practitioners in selecting and placing stents and other devices to restore or increase blood flow.

IVUS imaging systems includes a control module (with a pulse generator, an image acquisition and processing components, and a monitor), a catheter, and a transducer disposed in the catheter. The transducer-containing catheter is positioned in a lumen or cavity within, or in proximity to, a region to be imaged, such as a blood vessel wall or patient tissue in proximity to a blood vessel wall. The pulse generator in the control module generates electrical pulses that are delivered to the transducer and transformed to acoustic pulses that are transmitted through patient tissue. The patient tissue (or other structure) reflects the acoustic pulses and reflected pulses are absorbed by the transducer and transformed to electric pulses. The transformed electric pulses are delivered to the image acquisition and processing components and converted into images displayable on the monitor.

However, it can be difficult for physicians to visualize the complete structure of the patient lumen (e.g., vessel) from the raw IVUS images. For example, it is difficult to determine an overall plaque burden, the appropriate size of stent (e.g., diameter and/or length) to use in correcting any strictures in the lumen, as well as the location to land the stent. Thus, there is a need for systems and methods to process, annotate, visualize, and/or display images of a lumen of a patient based on IVUS images.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In general, the present disclosure provides to process raw IVUS images, automatically detected lumen and vessel borders, and identify regions of interest, or more particularly, starting and ending points between which include frames of interest in a series of IVUS images.

In some implementations, the present disclosure be embodied as a method, for example, a method for an intravascular ultrasound (IVUS) imaging system, comprising receiving a series of intravascular ultrasound (IVUS) images of a vessel of a patient, the series of IVUS images comprising a proximal IVUS frame, a distal IVUS frame, and a plurality of interior IVUS frames; determining a raw lumen area represented in each of the plurality of interior IVUS frames; generating, for each of the plurality of interior IVUS frames, a smooth lumen area based on a sampling filter and the lumen area; identifying as a smooth lumen frame, the one of the plurality of interior IVUS frames having a smooth lumen area less than or equal to the least smooth lumen area of the plurality interior IVUS frames; selecting a subset of the plurality of interior IVUS frames, the subset of interior IVUS frames comprising the smooth lumen frame and at least one other of the plurality of interior IVUS frames, wherein the smooth lumen frame and the at least one other of the plurality of interior IVUS frames are co-linear; and identifying as a minimum key frame, the one of the subset of the plurality of interior IVUS frames having a raw lumen area less than or equal to the lumen area of the subset of the plurality interior IVUS frames.

Alternatively, or additionally in any of the embodiments of a method above, the subset of the plurality of interior IVUS frames comprises 21 frames.

Alternatively, or additionally in any of the embodiments of a method above, the subset of the plurality of interior IVUS frames comprises ones of the series of IVUS images representing a distance along the vessel.

Alternatively, or additionally in any of the embodiments of a method above, the distance is less than or equal to 2 millimeters.

Alternatively, or additionally in any of the embodiments of a method above, the interior IVUS frames are disposed between the proximal IVUS frame and the distal IVUS frame.

Alternatively, or additionally in any of the embodiments of a method above, the series of IVUS images comprise a plurality of IVUS image frames and the method can comprise designating the first frame in the series of IVUS images as the distal key frame; and designating the last frame in the series of IVUS images as the proximal key frame.

Alternatively, or additionally any of the embodiments of a method above can comprise receiving, from an input device, an indication of the proximal IVUS frame and the distal IVUS frame.

Alternatively, or additionally in any of the embodiments of a method above, the series of IVUS images comprise a plurality of IVUS image frames and wherein identifying as the smooth lumen frame, the one of the plurality of interior IVUS frames having a smooth lumen area less than or equal to the smooth lumen area of the plurality interior IVUS frames can comprise designating each one of the plurality IVUS images disposed between the proximal IVUS frame and the distal IVUS frame as interior IVUS frames; identifying the least smooth lumen area of the plurality of interior IVUS frames; identifying the one or more of the plurality of interior IVUS frames having a smooth lumen area equal to the least smooth lumen area; and designating a one of the identified one or more of the plurality of interior IVUS frames disposed central to the proximal IVUS frame and the distal IVUS frame as the minimum smooth lumen frame.

Alternatively, or additionally in any of the embodiments of a method above, the sampling filter comprises a first sampling filter and the method can comprise generating, for each of the plurality of IVUS images, a smoother lumen area based on a second sampling filter and the smooth lumen area, wherein the second sampling filter is different than the first sampling filter.

Alternatively, or additionally in any of the embodiments of a method above, the series of IVUS images comprise a plurality of IVUS image frames and the method can comprise identifying an initial proximal search frame and an initial distal search frame; identifying an IVUS image frame from the one of the plurality of IVUS image frames located between the initial proximal search frame and the initial distal search frame having the smallest smoother lumen area; identifying, as a central search frame, the one of the plurality of IVUS image frames located within a first distance of the IVUS image frame having the smallest raw lumen area; identifying, as the distal key frame, the one of the plurality of IVUS image frames located within a second distance distal from the central search frame having a smooth plaque burden and a raw plaque burden less than a threshold value; and identifying, as the proximal key frame, the one of the plurality of IVUS image frames located within the second distance proximal from the central search frame having a smooth plaque burden and a raw plaque burden less than the threshold value.

Alternatively, or additionally in any of the embodiments of a method above, the threshold value is between 40 and 60 percent.

Alternatively, or additionally in any of the embodiments of a method above, the second distance is less than or equal to 5 millimeters.

Alternatively, or additionally in any of the embodiments of a method above, the first distance is less than or equal to 1 millimeter.

In some implementations, the present disclosure be embodied as an apparatus, comprising a processor of an intravascular ultrasound (IVUS) imaging system coupled to a memory, the memory comprising instructions executable by the processor, the processor configured to execute the instructions, which instructions when executed cause the processor to implement the method of any combination of the examples above.

In some implementations, the present disclosure can be embodied as at least one machine readable storage device, comprising a plurality of instructions that in response to being executed by a processor of an intravascular ultrasound (IVUS) imaging system cause the processor to implement the method of any combination of the examples above.

In some implementations, the present disclosure be embodied as an apparatus for an intravascular ultrasound (IVUS) imaging system, comprising circuitry to couple to an intravascular ultrasound (IVUS) system; a memory device storing instructions; and a processor coupled to the circuitry and the memory device, the processor configured to execute the instructions, which when executed cause the computing apparatus to: receive a series of intravascular ultrasound (IVUS) images of a vessel of a patient, the series of IVUS images comprising a proximal IVUS frame, a distal IVUS frame, and a plurality of interior IVUS frames; determine a raw lumen area represented in each of the plurality of interior IVUS frames; generate, for each of the plurality of interior IVUS frames, a smooth lumen area based on a sampling filter and the lumen area; identify as a smooth lumen frame, the one of the plurality of interior IVUS frames having a smooth lumen area less than or equal to the least smooth lumen area of the plurality interior IVUS frames; select a subset of the plurality of interior IVUS frames, the subset of interior IVUS frames comprising the smooth lumen frame and at least one other of the plurality of interior IVUS frames, wherein the smooth lumen frame and the at least one other of the plurality of interior IVUS frames are co-linear; and identify as a minimum key frame, the one of the subset of the plurality of interior IVUS frames having a raw lumen area less than or equal to the lumen area of the subset of the plurality interior IVUS frames.

Alternatively, or additionally in any of the embodiments of an apparatus above, the subset of the plurality of interior IVUS frames comprises 21 frames.

Alternatively, or additionally in any of the embodiments of an apparatus above, the subset of the plurality of interior IVUS frames comprises ones of the series of IVUS images represent a distance along the vessel.

Alternatively, or additionally in any of the embodiments of an apparatus above, the distance is less than or equal to 2 millimeters.

Alternatively, or additionally in any of the embodiments of an apparatus above, the interior IVUS frames are disposed between the proximal IVUS frame and the distal IVUS frame.

Alternatively, or additionally in any of the embodiments of an apparatus above, the series of IVUS images comprise a plurality of IVUS image frames and the memory device can further comprise instructions that when executed by the processor cause the IVUS imaging system to designate the first frame in the series of IVUS images as the distal key frame; and designate the last frame in the series of IVUS images as the proximal key frame.

Alternatively, or additionally in any of the embodiments of an apparatus above, the memory device can further comprise instructions that when executed by the processor cause the IVUS imaging system to receive, from an input device, an indication of the proximal IVUS frame and the distal IVUS frame.

Alternatively, or additionally in any of the embodiments of an apparatus above, the series of IVUS images comprise a plurality of IVUS image frames and wherein identifying as the smooth lumen frame, the one of the plurality of interior IVUS frames having a smooth lumen area less than or equal to the smooth lumen area of the plurality interior IVUS frames comprises: designate each one of the plurality IVUS images disposed between the proximal IVUS frame and the distal IVUS frame as interior IVUS frames; identify the least smooth lumen area of the plurality of interior IVUS frames; identify the one or more of the plurality of interior IVUS frames having a smooth lumen area equal to the least smooth lumen area; and designate a one of the identified one or more of the plurality of interior IVUS frames disposed central to the proximal IVUS frame and the distal IVUS frame as the minimum smooth lumen frame.

Alternatively, or additionally in any of the embodiments of an apparatus above, the sampling filter comprises a first sampling filter, the instructions when executed cause the computing apparatus to generate, for each of the plurality of IVUS images, a smoother lumen area based on a second sampling filter and the smooth lumen area, wherein the second sampling filter is different than the first sampling filter.

Alternatively, or additionally in any of the embodiments of an apparatus above, the series of IVUS images comprise a plurality of IVUS image frames and the memory device can further comprise instructions that when executed by the processor cause the IVUS imaging system to identify an initial proximal search frame and an initial distal search frame; identify an IVUS image frame from the one of the plurality of IVUS image frames located between the initial proximal search frame and the initial distal search frame having the smallest smoother lumen area; identify, as a central search frame, the one of the plurality of IVUS image frames located within a first distance of the IVUS image frame having the smallest raw lumen area; identify, as the distal key frame, the one of the plurality of IVUS image frames located within a second distance distal from the central search frame having a smooth plaque burden and a raw plaque burden less than a threshold value; and identify, as the proximal key frame, the one of the plurality of IVUS image frames located within the second distance proximal from the central search frame having a smooth plaque burden and a raw plaque burden less than the threshold value.

Alternatively, or additionally in any of the embodiments of an apparatus above, the threshold value is between 40 and 60 percent.

Alternatively, or additionally in any of the embodiments of an apparatus above, the first distance is less than or equal to 1 millimeter (mm) and the second distance is less than or equal to 5 mm.

In some implementations, the present disclosure can be embodied as at least one machine readable storage device, comprising a plurality of instructions that in response to being executed by a processor of an intravascular ultrasound (IVUS) imaging system cause the processor to receive a series of intravascular ultrasound (IVUS) images of a vessel of a patient, the series of IVUS images comprising a proximal IVUS frame, a distal IVUS frame, and a plurality of interior IVUS frames; determine a raw lumen area represented in each of the plurality of interior IVUS frames; generate, for each of the plurality of interior IVUS frames, a smooth lumen area based on a sampling filter and the lumen area; identify as a smooth lumen frame, the one of the plurality of interior IVUS frames having a smooth lumen area less than or equal to the least smooth lumen area of the plurality interior IVUS frames; select a subset of the plurality of interior IVUS frames, the subset of interior IVUS frames comprising the smooth lumen frame and at least one other of the plurality of interior IVUS frames, wherein the smooth lumen frame and the at least one other of the plurality of interior IVUS frames are co-linear; and identify as a minimum key frame, the one of the subset of the plurality of interior IVUS frames having a raw lumen area less than or equal to the lumen area of the subset of the plurality interior IVUS frames.

Alternatively, or additionally in any of the embodiments of an at least one machine readable storage device above, the subset of the plurality of interior IVUS frames comprises 21 frames.

Alternatively, or additionally in any of the embodiments of an at least one machine readable storage device above, the subset of the plurality of interior IVUS frames comprises ones of the series of IVUS images represent a distance along the vessel.

Alternatively, or additionally in any of the embodiments of an at least one machine readable storage device above, the distance is less than or equal to 2 millimeters.

Alternatively, or additionally in any of the embodiments of an at least one machine readable storage device above, the interior IVUS frames are disposed between the proximal IVUS frame and the distal IVUS frame.

Alternatively, or additionally in any of the embodiments of an at least one machine readable storage device above, the series of IVUS images comprise a plurality of IVUS image frames and the instructions in response to being executed by the processor can further cause the processor to designate the first frame in the series of IVUS images as the distal key frame; and designate the last frame in the series of IVUS images as the proximal key frame.

Alternatively, or additionally in any of the embodiments of an at least one machine readable storage device above, the instructions in response to being executed by the processor can further cause the processor to receive, from an input device, an indication of the proximal IVUS frame and the distal IVUS frame.

Alternatively, or additionally in any of the embodiments of an at least one machine readable storage device above, the series of IVUS images comprise a plurality of IVUS image frames and wherein identifying as the smooth lumen frame, the one of the plurality of interior IVUS frames having a smooth lumen area less than or equal to the smooth lumen area of the plurality interior IVUS frames comprises: designate each one of the plurality IVUS images disposed between the proximal IVUS frame and the distal IVUS frame as interior IVUS frames; identify the least smooth lumen area of the plurality of interior IVUS frames; identify the one or more of the plurality of interior IVUS frames having a smooth lumen area equal to the least smooth lumen area; and designate a one of the identified one or more of the plurality of interior IVUS frames disposed central to the proximal IVUS frame and the distal IVUS frame as the minimum smooth lumen frame.

BRIEF DESCRIPTION OF THE SEVERAL VIEWS OF THE DRAWINGS

To easily identify the discussion of any element or act, the most significant digit or digits in a reference number refer to the figure number in which that element is first introduced.

FIG. 3B illustrates an aspect of the subject matter in accordance with one embodiment.

FIG. 5 illustrates an aspect of the subject matter in accordance with one embodiment.

FIG. 7 illustrates an aspect of the subject matter in accordance with one embodiment.

FIG. 8 illustrates an aspect of the subject matter in accordance with one embodiment.

DETAILED DESCRIPTION

The foregoing has broadly outlined the features and technical advantages of the present disclosure such that the following detailed description of the disclosure may be better understood. It is to be appreciated by those skilled in the art that the embodiments disclosed may be readily utilized as a basis for modifying or designing other structures for carrying out the same purposes of the present disclosure. The novel features of the disclosure, both as to its organization and operation, together with further objects and advantages will be better understood from the following description when considered in connection with the accompanying figures. It is to be expressly understood, however, that each of the figures is provided for the purpose of illustration and description and is not intended as a definition of the limits of the present disclosure.

As noted, the present disclosure relates to IVUS images and lumens (e.g., vessels) of patients and to processing an IVUS recording, or said differently, processing a series of IVUS images. As such, an example IVUS imaging system, patient vessel, and series of IVUS images is described.

Suitable IVUS imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Numbers 2006/0100522; 2006/0106320; 2006/0173350; 2006/0253028; 2007/0016054; and 2007/0038111; all of which are incorporated herein by reference.

Figure 1:
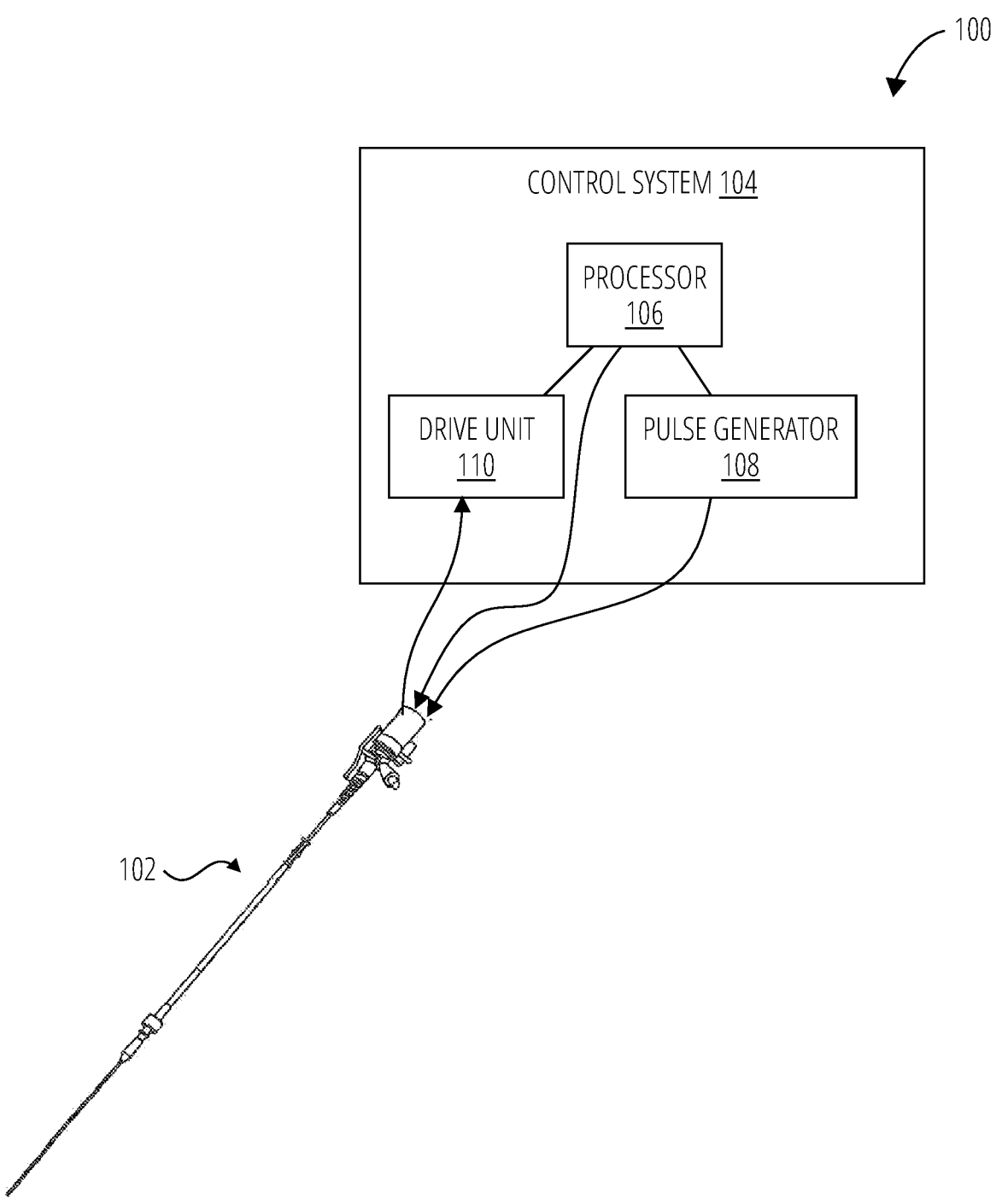
FIG. 1 illustrates an aspect of the subject matter in accordance with one embodiment.

FIG. 1 illustrates one embodiment of an IVUS imaging system 100. The IVUS imaging system 100 includes a catheter 102 that is couplable to a control system 104. The control system 104 may include, for example, a processor 106, a pulse generator 108, and a drive unit 110. The pulse generator 108 forms electric pulses that may be input to one or more transducers (not shown) disposed in the catheter 102.

With some embodiments, mechanical energy from the drive unit 110 can be used to drive an imaging core (also not shown) disposed in the catheter 102. In at least some embodiments, electric signals transmitted from the one or more transducers may be input to the processor 106 for processing. In at least some embodiments, the processed electric signals from the one or more transducers can be used to form a series of images, described in more detail below. For example, a scan converter can be used to map scan line samples (e.g., radial scan line samples, or the like) to a two-dimensional Cartesian grid, which can be used as the basis for a series of IVUS images that can be displayed for a user.

In at least some embodiments, the processor 106 may also be used to control the functioning of one or more of the other components of the control system 104. For example, the processor 106 may be used to control at least one of the frequency or duration of the electrical pulses transmitted from the pulse generator 108, the rotation rate of the imaging core by the drive unit 110. Additionally, where IVUS imaging system 100 is configured for automatic pullback, the drive unit 110 can control the velocity and/or length of the pullback.

Figure 2:
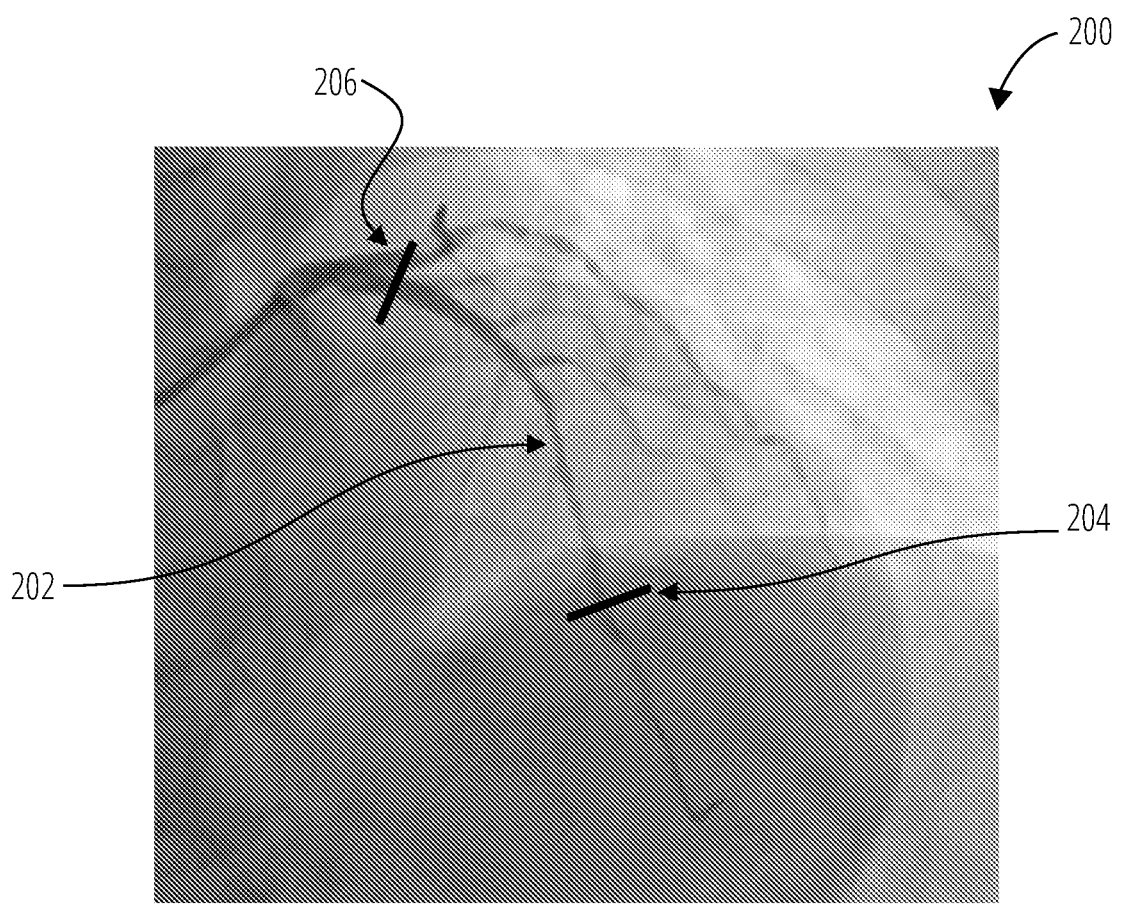
FIG. 2 illustrates an aspect of the subject matter in accordance with one embodiment.

FIG. 2 illustrates an image 200 of a vessel 202 of a patient. As described, IVUS imaging systems (e.g., IVUS imaging system 100, or the like) are used to capture a series of images or a "recording" or a vessel, such as, vessel 202. For example, an IVUS catheter (e.g., catheter 102) is inserted into vessel 202 and a recording, or a series of IVUS images, is captured as the catheter 102 is pulled back from a distal end 204 to a proximal end 206. The catheter 102 can be pulled back manually or automatically (e.g., under control of drive unit 110, or the like).

Figure 3A:
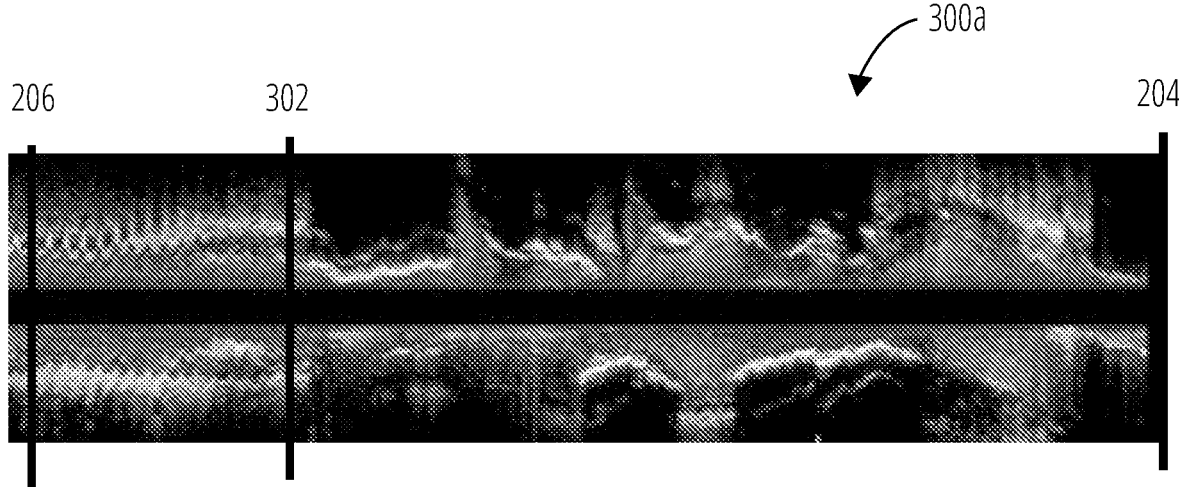
FIG. 3A illustrates an aspect of the subject matter in accordance with one embodiment.

FIG. 3A and FIG. 3B illustrates two-dimensional (2D) representations of IVUS images of vessel 202. For example, FIG. 3A illustrates IVUS images 300a depicting a longitudinal view of the IVUS recording of vessel 202 between proximal end 206 and distal end 204.

FIG. 3B illustrates an image frame 300b depicting an on-axis (or short axis) view of vessel 202 at point 302. Said differently, image frame 300b is a single frame or single image from a series of IVUS images that can be captured between distal end 204 and proximal end 206 as described herein. As introduced above, the present disclosure provides systems and techniques to process raw IVUS images to identify regions of interest, such as, for example starting and ending points between which include frames of interest in a series of IVUS images.

For example, IVUS images 300a depicts an entire series of IVUS images taken of vessel 202 between distal end 204 and proximal end 206. However, not all these images may be of interest to a physician. The present disclosure provides to identify "key frames" such as, a proximal key frame and a distal key frame as well as a minimum key frame.

Figure 4:
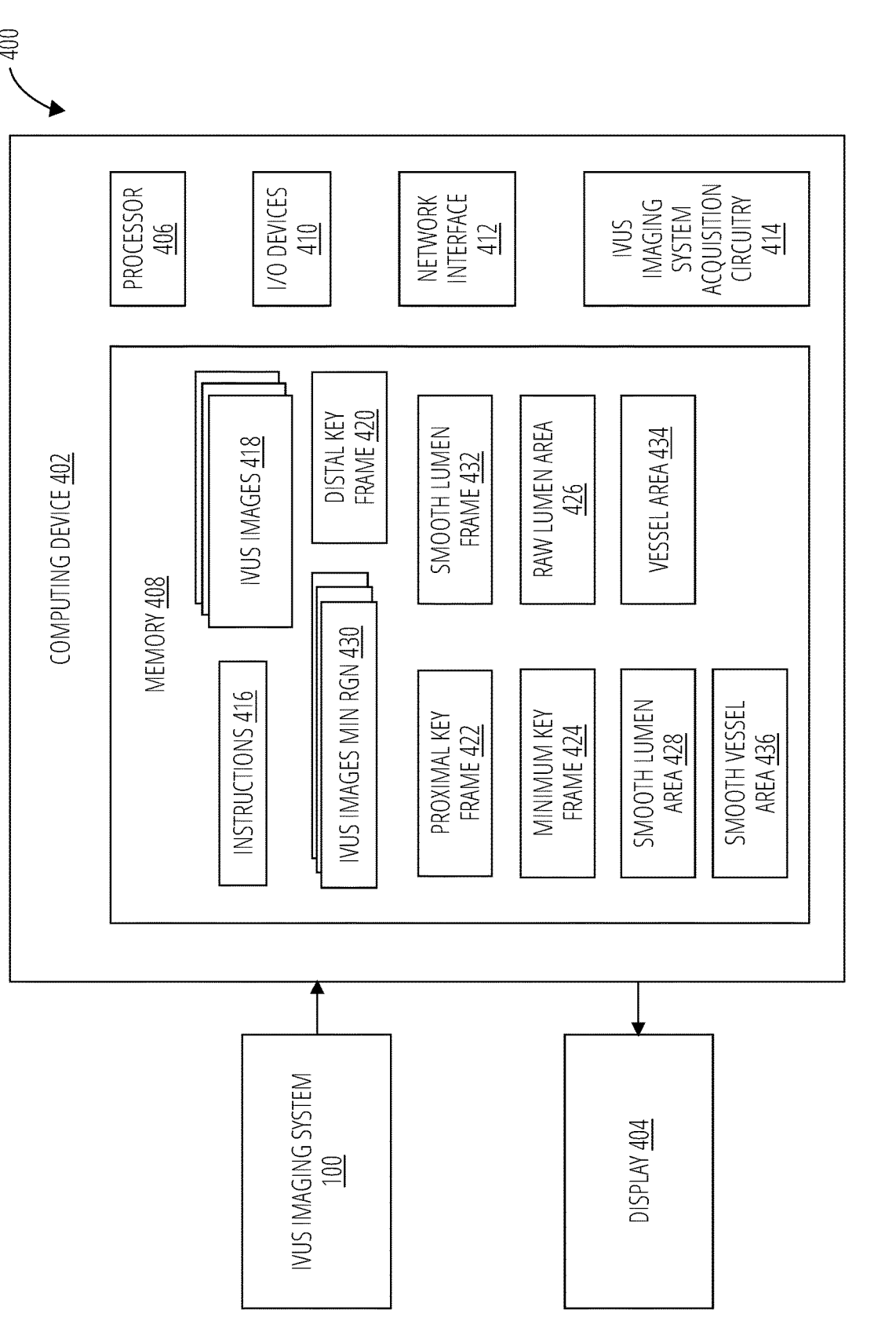
FIG. 4 illustrates IVUS images visualization system 400, in accordance with embodiment(s) of the present disclosure.

FIG. 4 illustrates an IVUS images visualization system 400, according to some embodiments of the present disclosure. In general, IVUS images visualization system 400 is a system for processing, annotating, and presenting IVUS images. IVUS images visualization system 400 can be implemented in a commercial IVUS guidance or navigation system, such as, for example, the AVVIGO® Guidance System available from Boston Scientific®. The present disclosure provides advantages over prior or conventional IVUS navigation systems in that the automatic detection of key frames will reduce the time needed for patients to be in treatment. For example, the present disclosure can be implemented in an IVUS navigation system used in a percutaneous coronary intervention (PCI). The disclosure can be provided to provide a physician rapidly and automatically with information including graphical information elements that provide more information than the raw IVUS images alone. This information (e.g., key frame identification and graphical representation) can be determined automatically as part of a pre-PCI, peri-PIC, or post-PCI while the user (e.g., physician, or the like) is using the system and while the patient is in treatment. For example, where the physician is placing a stent, the present disclosure can be used to present images to the physician (e.g., on a display) and provide a navigation framework for the physician to identify the type, size, and location of the stent more quickly and easily. Thereby reducing the time in which the patient is under treatment.

With some embodiments, IVUS images visualization system 400 could be implemented as part of control system 104. Alternatively, control system 104 could be implemented as part of IVUS images visualization system 400. As depicted, IVUS images visualization system 400 includes a computing device 402. Optionally, IVUS images visualization system 400 includes IVUS imaging system 100 and display 404.

Computing device 402 can be any of a variety of computing devices. In some embodiments, computing device 402 can be incorporated into and/or implemented by a console of display 404. With some embodiments, computing device 402 can be a workstation or server communicatively coupled to IVUS imaging system 100 and/or display 404. With still other embodiments, computing device 402 can be provided by a cloud based computing device, such as, by a computing as a service system accessibly over a network (e.g., the Internet, an intranet, a wide area network, or the like). Computing device 402 can include processor 406, memory 408, input and/or output (I/O) devices 410, network interface 412, and IVUS imaging system acquisition circuitry 414.

The processor 406 may include circuitry or processor logic, such as, for example, any of a variety of commercial processors. In some examples, processor 406 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 406 may include graphics processing portions and may include dedicated memory, multiple-threaded processing and/or some other parallel processing capability. In some examples, the processor 406 may be an application specific integrated circuit (ASIC) or a field programmable integrated circuit (FPGA).

The memory 408 may include logic, a portion of which includes arrays of integrated circuits, forming non-volatile memory to persistently store data or a combination of non-volatile memory and volatile memory. It is to be appreciated, that the memory 408 may be based on any of a variety of technologies. In particular, the arrays of integrated circuits included in memory 120 may be arranged to form one or more types of memory, such as, for example, dynamic random access memory (DRAM), NAND memory, NOR memory, or the like.

I/O devices 410 can be any of a variety of devices to receive input and/or provide output. For example, I/O devices 410 can include, a keyboard, a mouse, a joystick, a foot pedal, a display, a touch enabled display, a haptic feedback device, an LED, or the like.

Network interface 412 can include logic and/or features to support a communication interface. For example, network interface 412 may include one or more interfaces that operate according to various communication protocols or standards to communicate over direct or network communication links. Direct communications may occur via use of communication protocols or standards described in one or more industry standards (including progenies and variants). For example, network interface 412 may facilitate communication over a bus, such as, for example, peripheral component interconnect express (PCIe), non-volatile memory express (NVMe), universal serial bus (USB), system management bus (SMBus), SAS (e.g., serial attached small computer system interface (SCSI)) interfaces, serial AT attachment (SATA) interfaces, or the like. Additionally, network interface 412 can include logic and/or features to enable communication over a variety of wired or wireless network standards (e.g., 502.11 communication standards). For example, network interface 412 may be arranged to support wired communication protocols or standards, such as, Ethernet, or the like. As another example, network interface 412 may be arranged to support wireless communication protocols or standards, such as, for example, Wi-Fi, Bluetooth, ZigBee, LTE, 5G, or the like.

The IVUS imaging system acquisition circuitry 414 may include circuitry including custom manufactured or specially programmed circuitry configured to receive or receive and send signals between IVUS imaging system 100 including indications of an IVUS run, a series of IVUS images, or a frame or frames of IVUS images.

Memory 408 can include instructions 416. During operation processor 406 can execute instructions 416 to cause computing device 402 to receive (e.g., from IVUS imaging system 100, or the like) a recording of an "IVUS run" and store the recording as IVUS images 418 in memory 408. For example, processor 406 can execute instructions 416 to receive information elements from IVUS imaging system 100 comprising indications of IVUS images captured by catheter 102 while being pulled back from distal end 204 to proximal end 206, which images comprising indications of the anatomy and/or structure of vessel 202 including vessel walls and plaque. It is to be appreciated that IVUS images 418 can be stored in a variety of image formats or even non-image formats or data structures that comprise indications of vessel 202. Further, IVUS images 418 includes several "frames" or individual images that, when represented co-linearly can be used to form an image of the vessel 202, such as, for example, as represented by IVUS images 300a and/or 300b.

The present disclosure provides to process IVUS images to identify key frames from the frames in IVUS images 418. For example, the present disclosure provides to identify a distal key frame 420, a proximal key frame 422, and a minimum key frame 424. Processor 406 can execute instructions 416 to identify the minimum key frame 424. In some instances, processor 406 can execute instructions 416 to further identify the distal key frame 420 and/or the proximal key frame 422. However, with other instances, processor 406 can execute instructions 416 to receive an indication (e.g., via I/O devices 410, or the like) of the distal key frame 420 and/or proximal key frame 422. In some embodiments, processor 406 can execute instructions 416 to identify distal key frame 420, proximal key frame 422, and minimum key frame 424. Subsequently, processor 406 can execute instructions 416 to receive an indication of an updated distal key frame 420 and/or proximal key frame 422 and can re-identify minimum key frame 424 based on the updated distal key frame 420 and/or proximal key frame 422 as outlined herein.

In general, processor 406 can execute instructions 416 to identify the key frames based on the raw lumen boundaries as well as smoothed lumen boundaries. More specifically, processor 406 can execute instructions 416 to determine raw lumen area 426 for frames in IVUS images 418. Further, processor 406 can execute instructions 416 to determine a smooth lumen area 428 from raw lumen area 426. With some embodiments, the smooth lumen area 428 can be determined based on a moving average filter or an n-sample median filter. As a specific example, processor 406 can execute instructions 416 to determine smooth lumen area 428 based on a 21-sample median filter applied to IVUS images 418 and raw lumen area 426. Further, with some embodiments, smooth lumen area 428 can be determined based on a first filter and a second filter where the first filter is an n-sample median filter, and the second filter is an n-distance median filter. This is described in greater detail below. However, in general, where IVUS images 418 are captured via a manual pullback operation, smooth lumen area 428 can be determined based on a single filter (e.g., n-sample median filter). Conversely, where IVUS images 418 are captured via an automatic pullback operation, smooth lumen area 428 can be determined based on multiple filters (e.g., n-sample median filter and n-distance median filter).

Processor 406 can execute instructions 416 to determine a minimum region subset of IVUS images 430 from the frames in IVUS images 418 located co-linearly between the distal key frame 420 and the proximal key frame 422 by identifying a smooth lumen frame 432 based on the smooth lumen areas 428 and then identify the minimum key frame 424 from the frames in the minimum region subset of IVUS images 430 based on the raw lumen area 426. This provides an advantage in that errors in processing IVUS images 418 and determining raw lumen area 426 (e.g., automatic border detection errors, or the like) do not lead to mis-identification of minimum key frame 424.

In some embodiments, processor 406 can execute instructions 416 to identify the distal key frame 420 and the proximal key frame 422 based on a plaque burden, or rather, a ratio of raw lumen area 426 to vessel area 434. In such examples, processor 406 can execute instructions 416 to determine vessel area 434 for frames in IVUS images 418 and determine the distal key frame 420 and the proximal key frames 422 based on a ratio of raw lumen area 426 over vessel area 43 or of the smooth lumen areas 428 over the smooth vessel areas 436. This is described in greater detail below.

FIG. 5 illustrates a logic flow 500 to identify key frames from an IVUS recording, according to some embodiments of the present disclosure. The logic flow 500 can be implemented by IVUS images visualization system 400 and will be described with reference to IVUS images visualization system 400 for clarity of presentation. However, it is noted that logic flow 500 could also be implemented by an IVUS guidance system different than IVUS images visualization system 400.

Logic flow 500 can begin at block 502. At block 502 "receive a series of intravascular ultrasound (IVUS) images of a vessel of a patient" a series of IVUS images captured via an IVUS catheter percutaneously inserted in a vessel of a patent can be received. For example, information elements comprising indications of IVUS images 418 can be received from IVUS imaging system 100 where catheter 102 is (or was) percutaneously inserted into vessel 202. The IVUS images 418 can comprise frames of images representative of images captured while the catheter 102 is pulled back from distal end 204 to proximal end 206. Processor 406 can execute instructions 416 to receive information elements comprising indications of IVUS images 418 from IVUS imaging system 100, or directly from catheter 102 as may be the case.

Continuing to block 504 "determine a lumen area represented in each of the IVUS images" a lumen area represented in each frame of the IVUS images can be determined. For example, the raw lumen area 426 represented in each frame of the IVUS images 418 can be determined. Processor 406 can execute instructions 416 to determine raw lumen area 426 for IVUS images 418. Further, with some embodiments, at block 504 processor 406 can execute instructions 416 to determine vessel area 434 for IVUS images 418.

Figure 6:
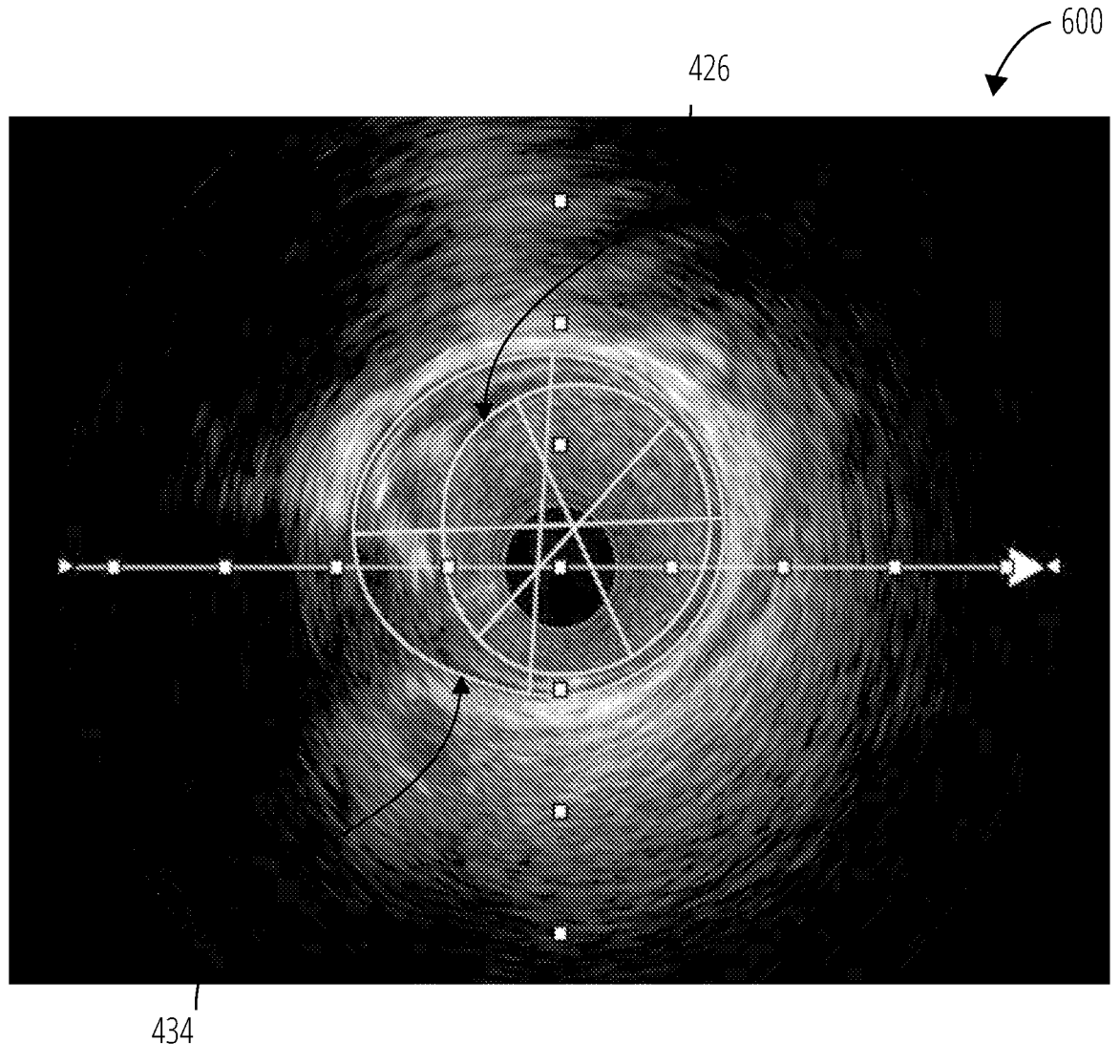
FIG. 6 illustrates an aspect of the subject matter in accordance with one embodiment.

For example, FIG. 6 illustrates an image 600 showing an on-axis view of a frame of IVUS images 418 depicting a portion of vessel 202. Vessel area 434 and raw lumen area 426 can be determined for the portion of vessel 202 represented in the depicted frame. Continuing to block 506 "smooth the raw lumen area" the raw lumen areas can be smoothed. For example, the raw lumen areas can be smoothed. In some embodiments, processor 406 can execute instructions 416 to determine smooth lumen areas 428 based on raw lumen areas 426 and an n-sample median filter. Smooth lumen areas 428 can be based on a 21-sample median filter applied to raw lumen areas 426. With other embodiments, processor 406 can execute instructions 416 to determine smooth lumen areas 428 based on raw lumen areas 426 and an n-sample median filter as well as an n-distance median filter. For example, smooth lumen areas 428 can be determined from raw lumen areas 426 and an n-sample median filter (e.g., 21-sample, or the like). Subsequently, "smoother" smooth lumen areas 428 can be determined from the smooth lumen areas 428 and an n-distance median filter. The n-distance median filter can be a 1 millimeter (mm) median filter, a 2 mm median filter, a 3 mm median filter, or a 4 mm median filter. It is noted that the "smoother" smooth lumen areas 428 can be used where the IVUS images 418 are based on an automatic pullback IVUS run.

Continuing to decision block 508 "distal and proximal key frames known" a determination of whether the distal key frame 420 and proximal key frame 422 are known is made. For example, processor 406 can execute instructions 416 to determine whether indications of the distal key frame 420 and proximal key frame 422 have been received (e.g., via I/O devices 410, or the like). From decision block 508, logic flow 500 can continue to either block 510 or proceed to block 512. Logic flow 500 can continue from decision block 508 to block 510 based on a determination at decision block 508 that the distal key frame 420 and proximal key frame 422 are unknown while logic flow 500 can proceed from decision block 508 to block 512 based on a determination at decision block 508 that the distal key frame 420 and proximal key frame 422 are known.

At block 510 "identify distal key frame and/or proximal key frame" the distal key frame 420 and/or the proximal key frame 422 can be determined. In some examples, both the distal key frame 420 and the proximal key frame 422 can be determined at block 510. In some instances, an indication of one of the key frames (e.g., distal key frame 420 or proximal key frame 422) may have been received and as such, the other key frame can be identified at block 510. In general, the distal key frame 420 and the proximal key frame 422 can be identified based in part on the smooth lumen area 428. However, specific examples of determining the distal key frame 420 and the proximal key frame 422 are provided below. For example, FIG. 7 and FIG. 8 depict logic flows 700 and 800, respectively, which can be implemented to identify the distal key frame 420 and the proximal key frame 422 for IVUS images 418 captured based on a manual pullback IVUS run (e.g., logic flow 700) or an automatic pullback IVUS run (e.g., logic flow 800).

Continuing to block 512 "identify a smooth lumen frame from the IVUS images" a frame from the series of IVUS images can be identified and designated as the smooth lumen frame. For example, processor 406 can execute instructions 416 to identify smooth lumen frame 432 from IVUS images 418 based on the distal key frame 420, proximal key frame 422, and smooth lumen areas 428 of each IVUS images 418. With some embodiments, processor 406 can execute instructions 416 to identify the frame of IVUS images 418 located between distal key frame 420 and proximal key frame 422 that has the smallest smooth lumen area 428. Where multiple frames of IVUS images 418 all have equal smooth lumen areas 428, which are the smallest smooth lumen area 428, processor 406 can identify the middle frame as the smooth lumen frame 432.

Continuing to block 514 "identify a subset of the IVUS images, the subset comprising the smooth lumen frame and a number of co-linear frames" a subset of the IVUS images can be identified. More particularly, the minimum region subset of IVUS images 430 can be determined from IVUS images 418 based on the smooth lumen frame 432. For example, processor 406 can execute instructions 416 to identify several frames of IVUS images 418 (at least 2, at least 11, several frames representing a selected distance along vessel 202, or the like) that are co-linearly located with the smooth lumen frame 432.

With some embodiments, for example, where IVUS images 418 are captured based on a manual pullback IVUS run, processor 406 can execute instructions 416 to identify the minimum region subset of IVUS images 430 based on identifying (or designating, marking, or flagging) the smooth lumen frame 432 as well as the m (e.g., 10, between 5 and 15, or the like) frames co-linearly distal and co-linearly proximal to the smooth lumen frame as the minimum region subset of IVUS images 430.

In some embodiments, for example, where IVUS images 418 are captured based on an automatic pullback IVUS run, processor 406 can execute instructions 416 to identify the minimum region subset of IVUS images 430 based on identifying (or designating, marking, or flagging) the smooth lumen frame 432 as well as the frames from IVUS images 418 that are captured within x distance (e.g., 1 mm, 1.5 mm, 2 mm, between 0.5 and 2 mm, or the like) of the smooth lumen frame 432 as the minimum region subset of IVUS images 430.

In some embodiments, where the distal key frame 420 or the proximal key frame 422 would be identified as being included in the minimum region subset of IVUS images 430, the minimum region subset of IVUS images 430 can be truncated to the frame just distal to the proximal key frame 422 or just proximal to the distal key frame 420.

Continuing to block 516 "identify a minimum key frame from the subset of the plurality of IVUS images" the frame with the smallest lumen area, or the minimum key frame, can be identified from the subset of the IVUS images and the raw lumen areas. For example, the minimum key frame 424 can be identified from the smooth lumen frame 432 based on the raw lumen areas 426. Processor 406 can execute instructions 416 to identify the frame from within the minimum region subset of IVUS images 430 that has the smallest raw lumen area 426.

FIG. 7 illustrates the logic flow 700, which can be implemented to identify the distal key frame 420 and/or the proximal key frame 422 for IVUS images 418 captured based on a manual IVUS run. As noted above, with some embodiments, logic flow 500 can implement logic flow 700 at block 510. Logic flow 700 can begin at block 702. At block 702 "identify the first frame in the recording as the distal key frame" the first frame in the IVUS recording can be designated or identified as the distal key frame. For example, processor 406 can execute instructions 416 to identify the first frame of the IVUS images 418 as the distal key frame 420. Continuing to block 704 "identify the last frame in the recording as the proximal key frame" the last frame in the IVUS recording can be designated or identified as the proximal key frame. For example, processor 406 can execute instructions 416 to identify the last frame of the IVUS images 418 as the proximal key frame 422.

FIG. 8 illustrates the logic flow 800, which can be implemented to identify the distal key frame 420 and/or the proximal key frame 422 based on the smooth lumen area 428 for IVUS images 418 captured based on a manual IVUS run. As noted above, with some embodiments, logic flow 500 can implement logic flow 800 at block 510. Logic flow 800 can begin at block 802. At block 802 "identify an initial distal search frame" an initial distal search frame can be identified. For example, processor 406 can execute instructions 416 to identify an initial distal search frame as either (1) the first frame in the series of IVUS images 418 or (2) the most distal frame in the series of IVUS images 418 where the smooth lumen area 428 less than or equal to the smooth lumen area 428 of the next distal frame plus 0.5 mm$^2$.

Continuing to block 804 "identify an initial proximal search frame" an initial proximal search frame can be identified. For example, processor 406 can execute instructions 416 to identify an initial proximal search frame as the frame that is most distal to (1) a specified distance (e.g., 1 mm, 1.1 mm, between 0.5 mm and 1.5 mm, or the like) distal to the last frame in the series of IVUS images 418, (2) the most proximal frame prior to the start of the guide catheter, or (3) consecutive frames with descending smooth lumen areas 428.

Continuing to block 806 "identify, as the central search frame, the frame between the initial proximal and distal search frames with the smallest raw lumen area located within a first distance from the frame with the smallest smooth lumen area" a central search frame can be identified as the frame between the initial proximal and distal search frames with the smallest raw lumen area located within a first distance from the frame with the smallest smooth lumen area. For example, processor 406 can execute instructions 416 to identify and designate as the central search frame the frame with the smallest raw lumen area 426 located within the first distance (e.g., 1 mm, 1.1 mm, between 0.5 mm and 1.5 mm, or the like) of the frame located between the initial proximal and distal search frames with the smallest smooth lumen area 428. As noted above, in some examples, the smooth lumen area can be determined based on multiple types of sampling filters. Said differently, a smooth lumen area may be determined, and a smoother lumen area may be determined. With some examples, the central search frame identified at block 806 can be identified based on the smoother lumen area and the raw lumen area as described above.

Continuing to block 808 "smooth the vessel area" the vessel area can be smoothed. For example, the processor 406 can execute instructions 416 to determine the smooth vessel areas 436 based on vessel areas 434 and an n-sample median filter. Continuing to block 810 "identify, as the distal and proximal key frames, the frames at least a second distance away from the central search frame with a smooth and a raw plaque burden less than or equal to a threshold" the distal and proximal key frames can be identified as the most proximate frames to the central search frame having a smooth and a raw plaque burden less than or equal to 50%. Processor 406 can execute instructions 416 to identify the distal key frame 420 as the frame at least a specified distance distal to the central search frame that has a smooth plaque burden (e.g., smooth lumen area 428 over smooth vessel area 436) less than or equal to a threshold (e.g., 50%, 60%, between 40 and 60%, or the like). In some examples, processor 406 can execute instructions 416 to determine that no frame distal to the central search frame has a raw and smooth plaque burden less than or equal to 50% and in such a case identify the initial distal search frame as the distal key frame 420.

Similarly, processor 406 can execute instructions 416 to identify the proximal key frame 422 as the frame at least a specified distance proximal to the central search frame that has a smooth plaque burden (e.g., smooth lumen area 428 over smooth vessel area 436) less than or equal to a threshold (e.g., 50%, 60%, between 40 and 60%, or the like). In some examples, processor 406 can execute instructions 416 to determine that no frame proximal to the central search frame has a raw and smooth plaque burden less than or equal to 50% and in such a case identify either (1) the last frame in the run or (2) the frame just distal to the guide catheter, whichever is more distal, as the proximal key frame 422.

Figure 9:
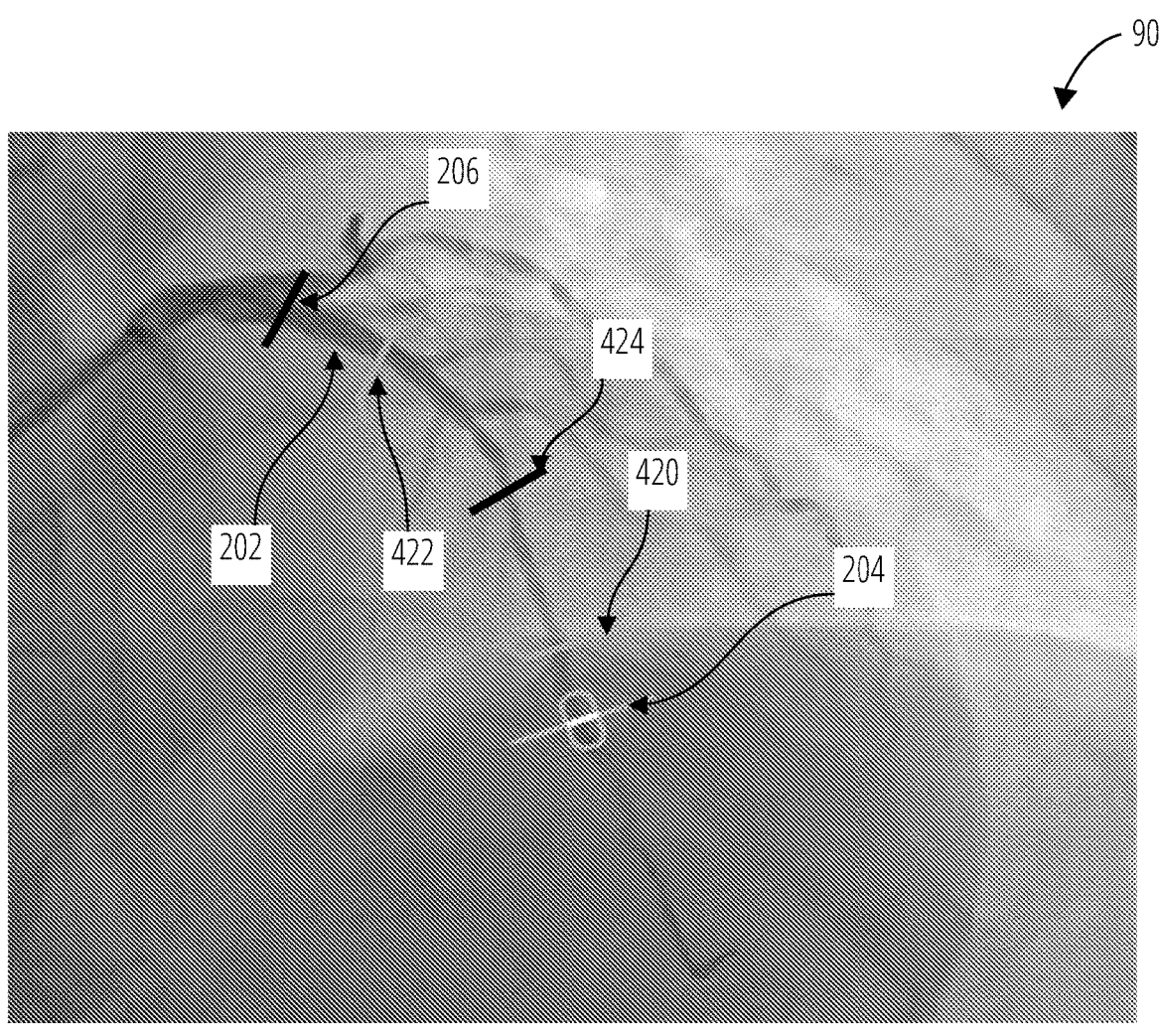
FIG. 9 illustrates an aspect of the subject matter in accordance with one embodiment.

FIG. 9 illustrates an annotated image 900 representative of an annotation of the image 200 depicting vessel 202, according to some embodiments of the present disclosure. As described herein, the present disclosure provides systems and techniques to automatically (e.g., without user input) identify key frames such as, the distal key frame 420, proximal key frame 422, and minimum key frame 424. With some examples, an image of the vessel 202 of the patient can be annotated with indications of the key frames as well as the start frames of the IVUS run. For example, processor 406 can execute instructions 416 to generate a graphical information element to be rendered and displayed on display 404 that represents annotated image 900. As depicted, the annotated image 900 includes a depiction of the vessel 202, the distal end 204, the proximal end 206, the distal key frame 420, the proximal key frame 422, and the minimum key frame 424.

Figure 10:
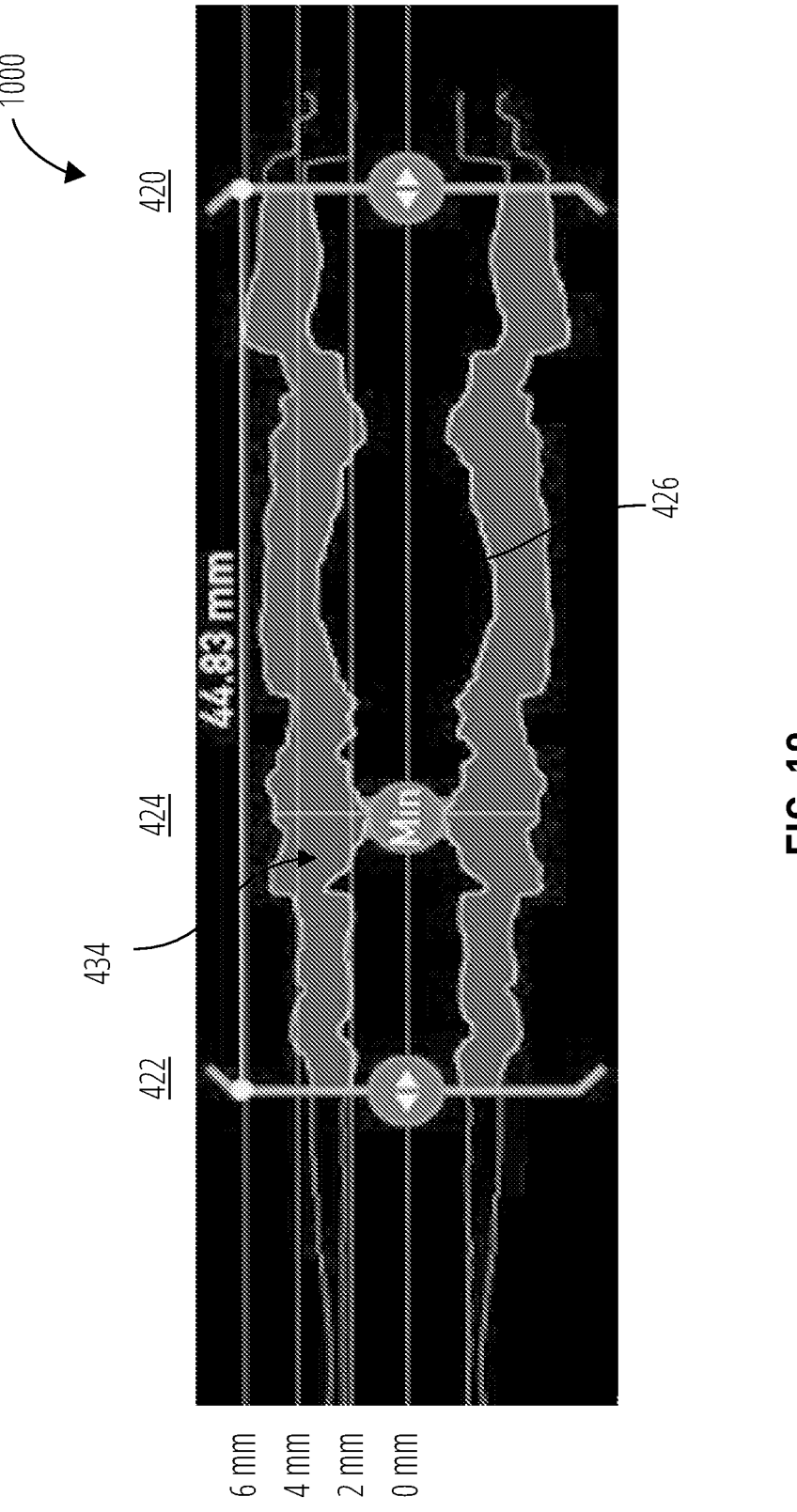
FIG. 10 illustrates an aspect of the subject matter in accordance with one embodiment.

FIG. 10 illustrates graphical element 1000, which can be generated and presented to a user according to some embodiments of the present disclosure. Processor 406 can execute instructions 416 to generate the graphical element 1000 including a cartoon depiction of the vessel area 434 and the raw lumen area 426 as well as the distal key frame 420, proximal key frame 422, and minimum key frame 424.

Annotated image 900 depicted in FIG. 9 and/or graphical element 1000 depicted in FIG. 10 can be generated by IVUS images visualization system 400 and displayed on display 404 as part of a PCI as outlined above.

Figure 11:
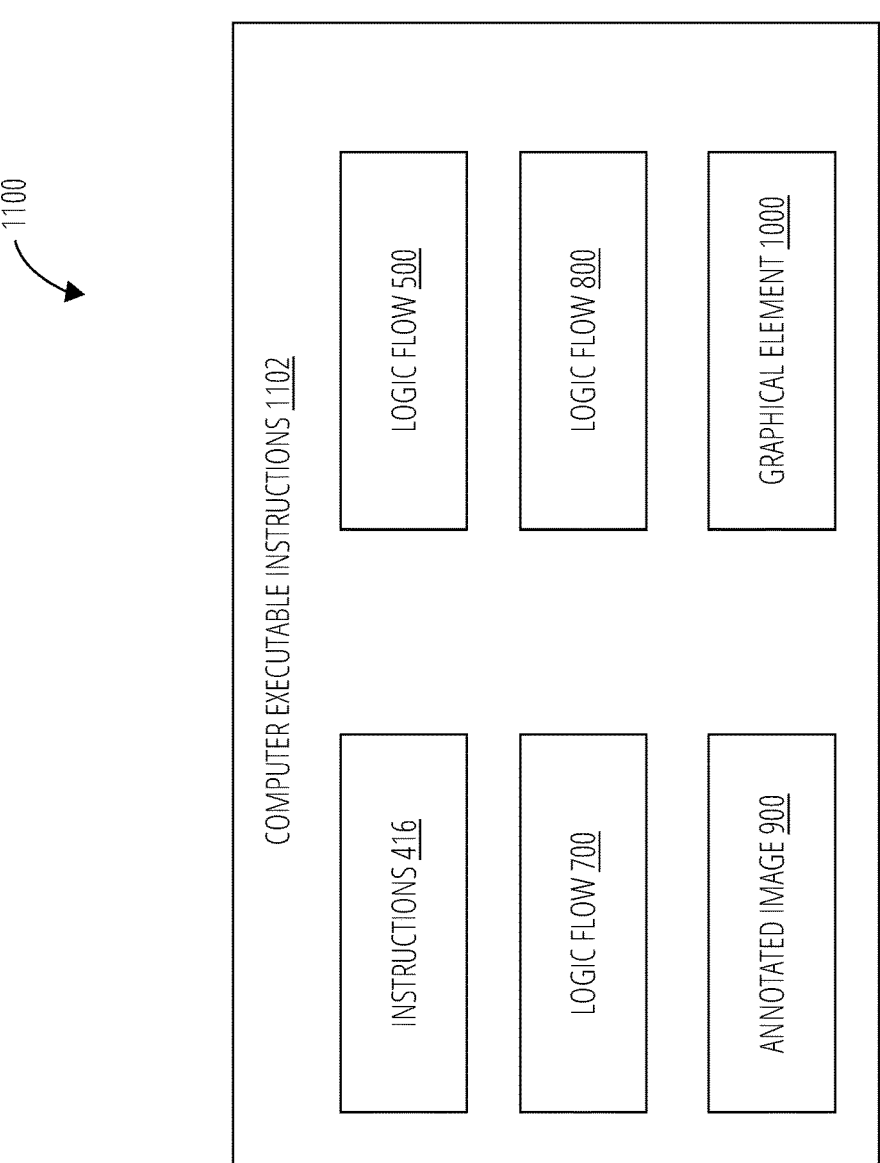
FIG. 11 illustrates a computer-readable storage medium 1100 in accordance with one embodiment.

FIG. 11 illustrates computer-readable storage medium 1100. Computer-readable storage medium 1100 may comprise any non-transitory computer-readable storage medium or machine-readable storage medium, such as an optical, magnetic or semiconductor storage medium. In various embodiments, computer-readable storage medium 1100 may comprise an article of manufacture. In some embodiments, computer-readable storage medium 1100 may store computer executable instructions 1102 with which circuitry (e.g., processor 106, processor 406, IVUS imaging system acquisition circuitry 414, and the like) can execute. For example, computer executable instructions 1102 can include instructions to implement operations described with respect to instructions 416, logic flow 500, logic flow 700, logic flow 800, annotated image 900, and/or graphical element 1000. Examples of computer-readable storage medium 1100 or machine-readable storage medium may include any tangible media capable of storing electronic data, including volatile memory or non-volatile memory, removable or non-removable memory, erasable or non-erasable memory, writeable or re-writeable memory, and so forth. Examples of computer executable instructions 1102 may include any suitable type of code, such as source code, compiled code, interpreted code, executable code, static code, dynamic code, object-oriented code, visual code, and the like.

Figure 12:
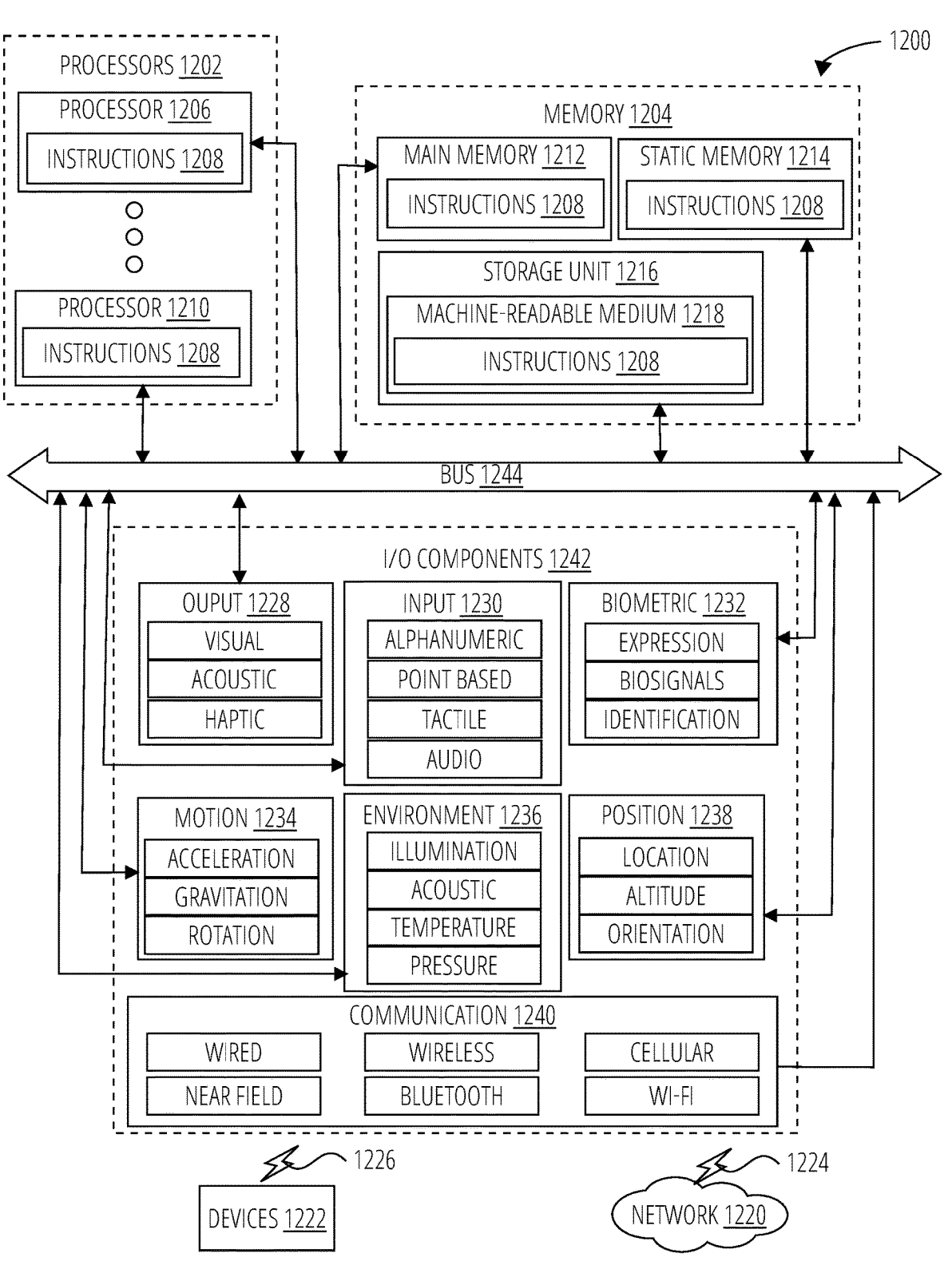
FIG. 12 illustrates a diagrammatic representation of a machine 1200 in the form of a computer system within which a set of instructions may be executed for causing the machine to perform any one or more of the methodologies discussed herein, according to an example embodiment.

FIG. 12 illustrates a diagrammatic representation of a machine 1200 in the form of a computer system within which a set of instructions may be executed for causing the machine to perform any one or more of the methodologies discussed herein. More specifically, FIG. 12 shows a diagrammatic representation of the machine 1200 in the example form of a computer system, within which instructions 1208 (e.g., software, a program, an application, an applet, an app, or other executable code) for causing the machine 1200 to perform any one or more of the methodologies discussed herein may be executed. For example, the instructions 1208 may cause the machine 1200 to execute logic flow 500 of FIG. 5, logic flow 700 of FIG. 7, logic flow 800 of FIG. 8, or the like. More generally, the instructions 1208 may cause the machine 1200 to automatically determine key frames during a pre-PCI, peri-PCI, or post-PCI using IVUS. It is noted that the present disclosure provides specific and discrete implementations of identifying key frames (e.g., distal key frame 420, proximal key frame 422, and/or minimum key frame 424) which is a significant improvement over the prior art. In particular, the present disclosure provides an improvement to computing technology in that key frames (e.g., particularly the minimum key frame 424) is identified while an IVUS imaging system is in use and can be re-identified based on updated factors (e.g., a user moving the distal key frame 420 or proximal key frame 422).

The instructions 1208 transform the general, non-programmed machine 1200 into a particular machine 1200 programmed to carry out the described and illustrated functions in a specific manner. In alternative embodiments, the machine 1200 operates as a standalone device or may be coupled (e.g., networked) to other machines. In a networked deployment, the machine 1200 may operate in the capacity of a server machine or a client machine in a server-client network environment, or as a peer machine in a peer-to-peer (or distributed) network environment. The machine 1200 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1208, sequentially or otherwise, that specify actions to be taken by the machine 1200. Further, while only a single machine 1200 is illustrated, the term "machine" shall also be taken to include a collection of machines 1200 that individually or jointly execute the instructions 1208 to perform any one or more of the methodologies discussed herein.

The machine 1200 may include processors 1202, memory 1204, and I/O components 1242, which may be configured to communicate with each other such as via a bus 1244. In an example embodiment, the processors 1202 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 1206 and a processor 1210 that may execute the instructions 1208. The term "processor" is intended to include multi-core processors that may comprise two or more independent processors (sometimes referred to as "cores") that may execute instructions contemporaneously. Although FIG. 12 shows multiple processors 1202, the machine 1200 may include a single processor with a single core, a single processor with multiple cores (e.g., a multi-core processor), multiple processors with a single core, multiple processors with multiples cores, or any combination thereof.

The memory 1204 may include a main memory 1212, a static memory 1214, and a storage unit 1216, both accessible to the processors 1202 such as via the bus 1244. The main memory 1204, the static memory 1214, and storage unit 1216 store the instructions 1208 embodying any one or more of the methodologies or functions described herein. The instructions 1208 may also reside, completely or partially, within the main memory 1212, within the static memory 1214, within machine-readable medium 1218 within the storage unit 1216, within at least one of the processors 1202 (e.g., within the processor's cache memory), or any suitable combination thereof, during execution thereof by the machine 1200.

The I/O components 1242 may include a wide variety of components to receive input, provide output, produce output, transmit information, exchange information, capture measurements, and so on. The specific I/O components 1242 that are included in a particular machine will depend on the type of machine. For example, portable machines such as mobile phones will likely include a touch input device or other such input mechanisms, while a headless server machine will likely not include such a touch input device. It will be appreciated that the I/O components 1242 may include many other components that are not shown in FIG. 12. The I/O components 1242 are grouped according to functionality merely for simplifying the following discussion and the grouping is in no way limiting. In various example embodiments, the I/O components 1242 may include output components 1228 and input components 1230. The output components 1228 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1230 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 1242 may include biometric components 1232, motion components 1234, environmental components 1236, or position components 1238, among a wide array of other components. For example, the biometric components 1232 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1234 may include acceleration sensor components (e.g., accelerometer), gravitation sensor components, rotation sensor components (e.g., gyroscope), and so forth. The environmental components 1236 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1238 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1242 may include communication components 1240 operable to couple the machine 1200 to a network 1220 or devices 1222 via a coupling 1224 and a coupling 1226, respectively. For example, the communication components 1240 may include a network interface component or another suitable device to interface with the network 1220. In further examples, the communication components 1240 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1222 may be another machine or any of a wide variety of peripheral devices (e.g., a peripheral device coupled via a USB).

Moreover, the communication components 1240 may detect identifiers or include components operable to detect identifiers. For example, the communication components 1240 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1240, such as location via Internet Protocol (IP) geolocation, location via Wi-Fi® signal triangulation, location via detecting an NFC beacon signal that may indicate a particular location, and so forth.

The various memories (i.e., memory 1204, main memory 1212, static memory 1214, and/or memory of the processors 1202) and/or storage unit 1216 may store one or more sets of instructions and data structures (e.g., software) embodying or utilized by any one or more of the methodologies or functions described herein. These instructions (e.g., the instructions 1208), when executed by processors 1202, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

In various example embodiments, one or more portions of the network 1220 may be an ad hoc network, an intranet, an extranet, a Virtual Private Network (VPN), a Local Area Network (LAN), a Wireless Local Area Network (WLAN), a Wide Area Network (WAN), a Wireless Wide Area Network (WWAN), a Metropolitan Area Network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 1220 or a portion of the network 1220 may include a wireless or cellular network, and the coupling 1224 may be a Code Division Multiple Access (CDMA) connection, a Global System for Mobile communications (GSM) connection, or another type of cellular or wireless coupling. In this example, the coupling 1224 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 1208 may be transmitted or received over the network 1220 using a transmission medium via a network interface device (e.g., a network interface component included in the communication components 1240) and utilizing any one of several well-known transfer protocols (e.g., hypertext transfer protocol (HTTP)). Similarly, the instructions 1208 may be transmitted or received using a transmission medium via the coupling 1226 (e.g., a peer-to-peer coupling) to the devices 1222. The terms "transmission medium" and "signal medium" mean the same thing and may be used interchangeably in this disclosure. The terms "transmission medium" and "signal medium" shall be taken to include any intangible medium that can store, encoding, or carrying the instructions 1208 for execution by the machine 1200, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. Any terms not expressly defined herein have their conventional meaning as commonly understood by those having skill in the relevant art(s).

By using genuine models of anatomy more accurate surgical plans may be developed than through statistical modeling.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. Any terms not expressly defined herein have their conventional meaning as commonly understood by those having skill in the relevant art(s).

What is claimed is:

1. A computing apparatus for an intravascular ultrasound (IVUS) system, comprising:

circuitry to couple to an intravascular ultrasound (IVUS) system;

a memory device storing instructions; and a processor coupled to the circuitry and the memory device, the processor configured to execute the instructions, which when executed cause the computing apparatus to:

receive a series of intravascular ultrasound (IVUS) images of a vessel of a patient, the series of IVUS images comprising a proximal IVUS frame, a distal IVUS frame, and a plurality of interior IVUS frames;

determine a raw lumen area represented in each of the plurality of interior IVUS frames;

generate, for each of the plurality of interior IVUS frames, a smooth lumen area based on a sampling filter and the raw lumen area;

identify as a smooth lumen frame, the one of the plurality of interior IVUS frames having a smooth lumen area less than or equal to the least smooth lumen area of the plurality of interior IVUS frames;

select a minimum region subset of the plurality of interior IVUS frames, the minimum region subset of interior IVUS frames comprising a series of adjacent interior IVUS frames comprising the smooth lumen frame and at least one other of the plurality of interior IVUS frames, wherein the smooth lumen frame and the at least one other of the plurality of interior IVUS frames are co-linear; and identify as a minimum key frame, the one of the minimum region subset of the plurality of interior IVUS frames having a raw lumen area less than or equal to the smallest raw lumen area among the minimum region subset of the plurality of interior IVUS frames.

2. The computing apparatus of claim 1, wherein the minimum region subset of the plurality of interior IVUS frames comprises 21 frames.

3. The computing apparatus of claim 1, wherein the minimum region subset of the plurality of interior IVUS frames comprises ones of the series of IVUS images representing a distance along the vessel.

4. The computing apparatus of claim 3, wherein the distance is less than or equal to 2 millimeters.

5. The computing apparatus of claim 1, wherein the interior IVUS frames are disposed between the proximal IVUS frame and the distal IVUS frame.

6. The computing apparatus of claim 1, wherein the series of IVUS images comprise a plurality of IVUS image frames, the instructions when executed cause the computing apparatus to:

designate the first frame in the series of IVUS images as the distal key frame; and designate the last frame in the series of IVUS images as the proximal key frame.

7. The computing apparatus of claim 1, the instructions when executed cause the computing apparatus to receive, from an input device, an indication of the proximal IVUS frame and the distal IVUS frame.

8. The computing apparatus of claim 7, wherein the series of IVUS images comprise a plurality of IVUS image frames and wherein identifying as the smooth lumen frame, the one of the plurality of interior IVUS frames having a smooth lumen area less than or equal to the smooth lumen area of the plurality interior IVUS frames comprises:

designate each one of the plurality IVUS images disposed between the proximal IVUS frame and the distal IVUS frame as interior IVUS frames;

identify the least smooth lumen area of the plurality of interior IVUS frames;

identify the one or more of the plurality of interior IVUS frames having a smooth lumen area equal to the least smooth lumen area; and designate a one of the identified one or more of the plurality of interior IVUS frames disposed central to the proximal IVUS frame and the distal IVUS frame as the minimum smooth lumen frame.

9. The computing apparatus of claim 1, wherein the sampling filter comprises a first sampling filter, the instructions when executed cause the computing apparatus to generate, for each of the plurality of IVUS images, a smoother lumen area based on a second sampling filter and the smooth lumen area, wherein the second sampling filter is different than the first sampling filter.

10. The computing apparatus of claim 1, wherein the series of IVUS images comprise a plurality of IVUS image frames, the instructions when executed cause the computing apparatus to:

identify an initial proximal search frame and an initial distal search frame;

identify an IVUS image frame from the one of the plurality of IVUS image frames located between the initial proximal search frame and the initial distal search frame having the smallest smoother lumen area;

identify, as a central search frame, the one of the plurality of IVUS image frames located within a first distance of the IVUS image frame having the smallest raw lumen area;

identify, as the distal key frame, the one of the plurality of IVUS image frames located within a second distance distal from the central search frame having a smooth plaque burden and a raw plaque burden less than a threshold value; and identify, as the proximal key frame, the one of the plurality of IVUS image frames located within the second distance proximal from the central search frame having a smooth plaque burden and a raw plaque burden less than the threshold value.

11. The computing apparatus of claim 10, wherein the threshold value is between 40 and 60 percent.

12. The computing apparatus of claim 10, wherein the first distance is less than or equal to 1 millimeter (mm) and wherein the second distance is less than or equal to 5 mm.

13. A non-transitory computer-readable storage medium, the computer-readable storage medium including instructions that when executed by a computer, cause the computer to:

receive a series of intravascular ultrasound (IVUS) images of a vessel of a patient, the series of IVUS images comprising a proximal IVUS frame, a distal IVUS frame, and a plurality of interior IVUS frames;

determine a raw lumen area represented in each of the plurality of interior IVUS frames;

generate, for each of the plurality of interior IVUS frames, a smooth lumen area based on a sampling filter and the lumen area;

identify as a smooth lumen frame, the one of the plurality of interior IVUS frames having a smooth lumen area less than or equal to the least smooth lumen area of the plurality of interior IVUS frames;

select a minimum region subset of the plurality of interior IVUS frames, the minimum region subset of interior IVUS frames comprising a series of adjacent interior IVUS frames comprising the smooth lumen frame and at least one other of the plurality of interior IVUS frames, wherein the smooth lumen frame and the at least one other of the plurality of interior IVUS frames are co-linear; and identify as a minimum key frame, the one of the minimum region subset of the plurality of interior IVUS frames having a raw lumen area less than or equal to the smallest raw lumen area among the minimum region subset of the plurality of interior IVUS frames.

14. The computer-readable storage medium of claim 13, wherein the minimum region subset of the plurality of interior IVUS frames comprises 21 frames.

15. The computer-readable storage medium of claim 13, wherein the minimum region subset of the plurality of interior IVUS frames comprises ones of the series of IVUS images representing a distance along the vessel.

16. The computer-readable storage medium of claim 15, wherein the distance is less than or equal to 2 millimeters.

17. The computer-readable storage medium of claim 13, wherein the interior IVUS frames are disposed between the proximal IVUS frame and the distal IVUS frame.

18. The computer-readable storage medium of claim 13, wherein the series of IVUS images comprise a plurality of IVUS image frames, the instructions when executed cause the computer to:

designate the first frame in the series of IVUS images as the distal key frame; and designate the last frame in the series of IVUS images as the proximal key frame.

19. The computer-readable storage medium of claim 13, the instructions when executed cause the computer to receive, from an input device, an indication of the proximal IVUS frame and the distal IVUS frame.

20. The computer-readable storage medium of claim 19, wherein the series of IVUS images comprise a plurality of IVUS image frames and wherein identifying as the smooth lumen frame, the one of the plurality of interior IVUS frames having a smooth lumen area less than or equal to the smooth lumen area of the plurality interior IVUS frames comprises:

designate each one of the plurality IVUS images disposed between the proximal IVUS frame and the distal IVUS frame as interior IVUS frames;

identify the least smooth lumen area of the plurality of interior IVUS frames;

identify the one or more of the plurality of interior IVUS frames having a smooth lumen area equal to the least smooth lumen area; and designate a one of the identified one or more of the plurality of interior IVUS frames disposed central to the proximal IVUS frame and the distal IVUS frame as the minimum smooth lumen frame.

\*   \*   \*   \*   \*